United States Patent [19]

Miyake et al.

[11] Patent Number: 5,928,206
[45] Date of Patent: Jul. 27, 1999

[54] MEDICAL DEVICE

[75] Inventors: Masao Miyake; Naomi Fujimori, both of Yokohama, Japan

[73] Assignee: Mitsubishi Chemical Corporation, Tokyo, Japan

[21] Appl. No.: 08/950,800

[22] Filed: Oct. 15, 1997

[30] Foreign Application Priority Data

Oct. 18, 1996 [JP] Japan ................................ 8-276299

[51] Int. Cl.$^6$ .............................. A01N 1/00; B32B 15/08
[52] U.S. Cl. ........................... 604/264; 623/1; 428/424.4
[58] Field of Search ................................... 604/264, 265; 623/1, 4, 8, 9, 11–14; 427/2.12, 2.13, 2.25, 333, 372.2, 337, 384, 385.5, 407.1, 393.5; 428/423.1, 423.4, 424.2, 424.4, 451, 476.3, 483, 520, 522

[56] References Cited

U.S. PATENT DOCUMENTS

| | | | |
|---|---|---|---|
| 4,074,039 | 2/1978 | Lim et al. | 623/1 |
| 4,373,009 | 2/1983 | Winn | 604/280 |
| 4,610,690 | 9/1986 | Tiffany | 623/8 |
| 4,743,258 | 5/1988 | Ikada et al. | 623/11 |
| 5,011,275 | 4/1991 | Mueller | 604/890.1 |
| 5,441,488 | 8/1995 | Shimura et al. | 604/265 |
| 5,670,558 | 9/1997 | Onishi et al. | 604/265 |
| 5,726,250 | 3/1998 | Zajaczkowski | 525/296 |
| 5,804,318 | 9/1998 | Pinchuk et al. | 623/2 |

*Primary Examiner*—Wynn Wood Coggins
*Assistant Examiner*—Sharon Finkel
*Attorney, Agent, or Firm*—Oblon, Spivak, McClelland, Maier & Neustadt, P.C.

[57] ABSTRACT

Disclosed is a medical device in which a surface of a base material for constructing the medical device is coupled to a high-molecular weight compound composed of N-substituted alkylacrylamide by the aid of a reaction between a reactive functional group such as isocyanate group, epoxy group, and aldehyde group existing on the surface and a functional group which is possessed by the high-molecular weight compound and which is reactive with the first reactive functional group.

12 Claims, No Drawings

MEDICAL DEVICE

TECHNICAL FIELD

The present invention relates to a medical device. In particular, the present invention relates to a medical device excellent in facile lubrication, having a coating which swells in the presence of an aqueous medium and which undergoes a decrease in the coefficient of friction in accordance therewith.

BACKGROUND OF THE INVENTION

Medical devices such as guide wires and various catheters, which have been hitherto used by being inserted or pierced into a living body, have a surface formed of a resin such as silicon resin, polyurethane, and vinyl chloride resin. When the medical device having a tubular or rod-shaped configuration provided with such a surface is inserted into the body, it is difficult to make insertion because of an extremely large frictional resistance. Therefore, problems arise, for example, in that the living body suffers from a great deal of pain, and mucous membrane and tissue are damaged.

In order to obviate on the foregoing drawbacks, it is known that the surface of the medical device as described above is treated such that a low friction material such as a fluororesin is used therefor, or a hydrophilic macromolecule or a lubricant such as Xylocaine jelly and olive oil is applied thereto. However, even when fluororesin is used, the friction is not sufficiently reduced when the medical device is inserted into the living body. When the lubricant is applied, the lubricant flows out within an extremely short period of time. Therefore, it is impossible to obtain a sufficient effect.

Taking notice of the fact that the hydrophilic high-molecular compound swells in the presence of an aqueous medium, and the coefficient of friction is decreased in accordance therewith, Japanese Laid-Open Patent Publication No. 6-7426 discloses that the surface of a medical device is coated, for example, with a polymer composed of maleic anhydride. However, in this method, the surface of the medical device is merely coated with the water-soluble macromolecule. Therefore, the hydrophilic macromolecule tends to be eluted from the surface, which is not desirable from a viewpoint of safety. Further, the effect to reduce the friction does not continue for a long period of time.

Japanese Laid-Open Patent Publication No. 3-184557 discloses that a hydrophilic vinyl monomer is graft-copolymerized on a surface layer of a medical device. In this method, the improvement is made in that the elution of the water-soluble macromolecule is suppressed, however, a product obtained by the graft polymerization does not have a high molecular weight. Therefore, it is impossible to obtain a sufficient effect to decrease the friction.

Each of Japanese Laid-Open Patent Publication Nos. 54-29343 and 58-193767 discloses a medical device coated with an N-vinylpyrrolidone polymer by the aid of an isocyanate group. However, a problem of elution of the polymer also arises.

Japanese Laid-Open Patent Publication No. 63-238170 discloses a medical device in which a copolymer composed of an active hydrogen-containing monomer and N-vinylpyrrolidone is coupled to a base material through an isocyanate group, and Japanese Patent Publication No. 1-33181 discloses a medical device in which a copolymer composed of maleic anhydride and methyl vinyl ether is coupled to a base material through an isocyanate group. The improvement is made from a viewpoint of elution, because these compounds form chemical bonds. However, the copolymer composed of maleic anhydride and methyl vinyl ether is hydrolyzed upon contact with water. As a result, maleic acid is produced from maleic anhydride, and the surface of the medical device becomes extremely strongly anionic. Therefore, the compound is not preferred from a viewpoint of biocompatibility. Further, the hydrophilic property is insufficient, and it is impossible to expect a sufficient effect to reduce the friction, because methyl vinyl ether which is not hydrophilic is contained in an amount of 50%. Both of the copolymer composed of the active hydrogen-containing monomer and N-vinylpyrrolidone and the copolymer composed of maleic acid and methyl vinyl ether have low flexibility, and hence they have low film strength. Accordingly, they have a drawback that the surface is easily peeled off when it undergoes friction.

As described above, the conventional method has failed to provide a medical material in which the coefficient of friction is safely reduced while suppressing the elution of macromolecule existing on the surface of the base material.

SUMMARY OF THE INVENTION

The present invention has been made taking the foregoing circumstances into consideration, an object of which is to provide a medical device in which the coefficient of friction is reduced in the presence of an aqueous medium, and the elution of a hydrophilic macromolecule existing on the surface of the medical device is suppressed, when the medical device is inserted or pierced into a living body.

As a result of investigations performed by the present inventors in order to achieve the object described above, it has been found out that a medical device, which is obtained by coupling a macromolecule composed of N-substituted alkylamide to a surface of a base material for constructing the medical device in accordance with a specified reaction, makes it possible to reduce the coefficient of friction upon insertion into a living body, and decrease the elution of the macromolecule existing on the surface of the base material. Thus, the present invention has been completed.

That is, according to the gist or feature of the present invention, there is provided a medical device comprising a base material for constructing the medical device, and a high-molecular weight compound composed of N-substituted alkylacrylamide coupled to a surface of the base material by the aid of chemical bond, wherein the chemical bond is formed by a reaction between a reactive functional group (hereinafter referred to as "first reactive functional group") which is selected from the group consisting of isocyanate group, epoxy group, and aldehyde group and a functional group (hereinafter referred to as "second reactive functional group") which is reactive with the first reactive functional group, the first reactive functional group originates from the surface of the base material, and the second reactive functional group originates from the high-molecular weight compound composed of the N-substituted alkylacrylamide.

The present invention will be explained in further detail below.

The medical device according to the present invention may be directed to any one of those contact with tissue of living bodies, mucous membrane, and blood. Those preferably directed are guide wires and catheters, and those more preferably directed are catheters.

Specifically, the catheter includes, for example, catheters to be orally or nasogastrically inserted into or retained at the inside of digestive tract, such as stomach tube catheter, nutrition catheter, and ED tube (for nutrition through tract); catheters to be inserted into or retained at the inside of trachea, such as oxygen catheter, oxygen cannula, intratracheal tube and cuff, tracheostomy tube, and intratracheal suction catheter; catheters to be inserted into or retained at the inside of urethra such as urine-introducing catheter and urethra catheter; catheters to be inserted into or retained at the inside of blood vessel, such as indwelling needle, IVH catheter, angiography catheter, thermodilution catheter, dilator, and introducer; and catheters to be inserted into or retained at the inside of various body cavities and tissues, such as suction catheter, discharge catheter, and rectum catheter.

In the present invention, it is necessary that the reactive functional group ("first reactive functional group") selected from the group consisting of isocyanate group, epoxy group, and aldehyde group exists on the surface of the base material for constructing the medical device.

In the present invention, it is necessary that the high-molecular weight compound composed of N-substituted alkylacrylamide is coupled to the surface of the base material for constructing the medical device through the chemical bond. The chemical bond results from, for example, the chemical reaction between the first reactive functional group selected from the group consisting of isocyanate group, epoxy group, and aldehyde group and the second reactive functional group which is reactive with the first reactive functional group. In this aspect, the first reactive functional group is allowed to exist on the surface of the base material, and the second reactive functional group is allowed to exist on the high-molecular compound weight composed of the N-substituted alkylacrylamide.

The method for allowing the first reactive functional group to exist on the surface of the base material for constructing the medical device includes, for example, a method in which the base material itself for constructing the medical device is previously produced by using the high-molecular weight compound-weight having the reactive functional group, and a method in which production is carried out by reacting the base material for constructing the medical device with a reactive substance having the first reactive functional group (hereinafter simply referred to as "reactive substance", if necessary). Especially, it is preferable to use the method in which the reactive substance is allowed to react with the base material for constructing the medical device.

Those usable as the reactive substance include, for example, polyisocyanates having two or more functional groups, epoxy group-containing compounds having reactive groups, and polyaldehydes having two or more functional groups. Especially, it is preferable to use the polyisocyanates having two or more functional groups.

The polyisocyanate includes, for example, ethylene diisocyanate, hexamethylene diisocyanate, xylene diisocyanate, toluene diisocyanate, diphenylmethane diisocyanate, naphthalene diisocyanate, phenylene diisocyanate, cyclohexylene diisocyanate, triphenylmethane triisocyanate, toluene triisocyanate, 4,4'-dicyclohexylmethane diisocyanate, 1-isocyanato-3-isocyanatomethyl-3,5,5-trimethylcyclohexane, and adducts and prepolymers of the polyisocyanates and polyols.

The epoxy group-containing compound having the reactivity includes, for example, diepoxybutane, 1,2-diepoxy-3-chloropropane.

The polyaldehyde includes, for example, terephthalaldehyde, isophthalaldehyde, glyoxal, starch, malonaldehyde, succinaldehyde, glutaraldehyde, and adipic aldehyde.

The reactive substance may be reacted with the base material for constructing the medical device as follows. That is, when the base material, which has a residue such as amino group on the surface, is used, the reactive substance may be reacted with the base material as it is, for example, by means of immersion. However, when the base material, which scarcely has such a residue on the surface, is used, a method is adopted, in which the base material is coated with a high-molecular compound having such a residue, and then the reactive substance is allowed to react therewith.

The residue is herein represented by a group which has the reactivity with the second reactive functional group described later on possessed by the high-molecular weight compound composed of N-substituted alkylacrylamide.

The base material having the residue includes, for example, those made of polyurethane and polyamide. The base material having no residue includes, for example, those made of polyethylene, polyvinyl chloride, fluororesin, and silicon. Those preferably used as the high-molecular weight compound containing the residue for coating the medical device having no residue therewith include, for example, polyurethane and polyamide.

In the present invention, the high-molecular weight compound composed of N-substituted alkylacrylamide has the functional group ("second reactive functional group") which is reactive with the first reactive functional group existing on the surface of the base material for constructing the medical device. Those preferably used as the high-molecular weight compound as described above include, for example, a copolymer of N-substituted alkylacrylamide and a monomer having the second reactive functional group (hereinafter referred to as "functional group-containing monomer", if necessary).

Those preferably used as N-substituted alkylacrylamide described above include those in which the alkyl group has a number of carbon or carbons of 1 to 4. Those more preferably used as N-substituted alkylacrylamide described above include N,N-dialkylacrylamide in which the alkyl group has a number of carbon or carbons of 1 to 4.

Specifically, the N-substituted alkylacrylamide as described above includes, for example, N-methylacrylamide, N-ethylacrylamide, N-propylacrylamide, N-butylacrylamide, N,N-dimethylacrylamide, and N,N-diethylacrylamide. Especially, N,N-dialkylacrylamide is preferably used. In particular, N,N-dimethylacrylamide is more preferably used.

The N-substituted alkylacrylamide may be used singly or in combination of two or more species. When two or more species of the N-substituted alkylacrylamides are used, one of them is preferably N,N-dialkylacrylamide.

The functional group-containing monomer includes, for example, vinyl type monomers having a functional group such as hydroxyl group, amino group, and carboxyl group. Specifically, for example, there are exemplified hydroxyethyl acrylate, hydroxyethyl methacrylate, and acrylamide. It is preferable to use hydroxyethyl methacrylate and hydroxyethyl acrylate. One of them may be used to provide the copolymer with N-substituted alkylacrylamide. Alternatively, two or more of them may be used.

The functional group-containing monomer is ordinarily contained in the high-molecular weight compound composed of N-substituted alkylacrylamide in a ratio of 0.01 to 15 mole %, preferably 0.01 to 8 mole %, and more preferably 0.05 to 5 mole %. If the ratio of the monomer is too small, the coupling becomes insufficient. If the ratio is too large, no sufficient hydration can be obtained, because the degree of freedom of the molecular chain is decreased. Further, the flexibility of a formed coating disappears, and hence the friction is not reduced sufficiently. Moreover, the film tends to be peeled of in some cases.

N-substituted alkylacrylamide and a monomer other than the functional group-containing monomer may be used together as constitutive components for the high-molecular weight compound composed of N-substituted alkylacrylamide. Such a monomer is not specifically limited provided that the monomer can be subjected to copolymerization. However, in order to improve the flexibility of the coating formed by the high-molecular weight compound composed of N-substituted alkylacrylamide, it is preferable to use a monomer having a property to give flexibility. When such a monomer is used together, it is possible to avoid occurrence of fine irregularities on the surface of the coating. The fine irregularities on the surface of the coating are not preferred, because they induce increase in frictional force as well as formation of thrombus.

Those used as the monomer having the property to add flexibility (hereinafter referred to as "flexibility-adding monomer", if necessary) includes, for example, diacetone acrylamide, acrylic acid, methacrylic acid, ester of acrylic acid and alcohol having a number of carbon or carbons of 1 to 12, ester of methacrylic acid and alcohol having a number of carbon or carbons of 1 to 12, and vinyl ester. The monomer may be used singly, or two or more of the monomers may be used in combination. Those preferably used as the ester of acrylic acid or methacrylic acid and alcohol having a number of carbon or carbons of 1 to 12 include ester of acrylic acid or methacrylic acid and alcohol having a number of carbon or carbons of 1 to 8. Specifically, there are exemplified ethyl acrylate, ethyl methacrylate, butyl acrylate, butyl methacrylate, methyl acrylate, and methyl methacrylate. The vinyl ester may be exemplified by vinyl acetate and vinyl propionate. Preferably, vinyl acetate is used. Among the monomers, it is preferable to use diacetone acrylamide, methyl methacrylate, and ethyl acrylate.

The monomer to give flexibility is ordinarily used in the high-molecular weight compound composed of N-substituted alkylacrylamide in a ratio of 0.01 to 10 mole %, and preferably 0.2 to 8 mole %. If the amount of the monomer is too small, it is impossible to sufficiently suppress formation of irregularities of the coating. If the amount of the monomer is too large, the monomer causes increase in friction in water in some cases.

The high-molecular weight compound composed of N-substituted alkylacrylamide is obtained by polymerizing N-substituted alkylacrylamide, the monomer having the second reactive functional group, and optionally the flexibility-adding monomer, in accordance with an ordinary method. For example, the high-molecular compound composed of N-substituted alkylacrylamide may be produced in accordance with any method such as anion polymerization, cation polymerization, and radical polymerization. Especially, radical polymerization is preferred. Radical polymerization may be performed, for example, in accordance with solution polymerization, emulsion polymerization, and pearl polymerization, by using a polymerization initiator of an azo compound such as azobisisobutyronitrile and 2,2'-azobis(2,4-dimethylvaleronitrile) or a peroxide such as benzoyl peroxide and t-butyl perpivalate. In order to obtain the high-molecular weight compound composed of N-substituted alkylacrylamide having a relatively low molecular weight, it is preferable to perform polymerization in a ketone solvent such as ethyl methyl ketone. In order to obtain the high-molecular weight compound composed of N-substituted alkylacrylamide having a relatively high molecular weight, it is preferable to perform polymerization in an aqueous solution or perform production in accordance with peal polymerization of the water-in-oil type.

Usually, those having a molecular weight of about ten thousands to ten millions are used as the high-molecular weight compound composed of N-substituted alkylacrylamide. Especially, those having a molecular weight of fifty thousands to six millions are preferably used.

When the coating of the high-molecular weight compound composed of N-substituted alkylacrylamide is formed on the base material having the residue described above, a method is used, in which the base material is coated with a solution of the reactive substance having the first reactive functional group, and then the base material is coated with a solution of the high-molecular weight compound composed of N-substituted alkylacrylamide, followed by performing a reaction to form the chemical bond. The solution of the reactive substance may contain other high-molecular weight compounds such as urethane.

When the coating of the high-molecular weight compound composed of N-substituted alkylacrylamide is formed on the base material having no residue, a method is used, in which the base material is coated with a solution obtained by dissolving, for example, polyurethane or polyamide, thereafter the base material is coated with the reactive substance, and then the base material is coated with the high-molecular weight compound composed of N-substituted alkylacrylamide, followed by performing a reaction to form the chemical bond.

Any solvent may be used when the base material is coated with the reactive substance provided that the solvent makes no reaction with the reactive substance. However, those usable as the solvent include, for example, ketone solvent such as acetone, methyl ethyl ketone, and methyl isobutyl ketone; halogen solvent such as methylene chloride and chloroform; ester solvent such as ethyl acetate and butyl acetate; and ether solvent such as tetrahydrofuran and dioxane. Especially, it is preferable to use the ketone solvent, the halogen solvent, or a mixture thereof, because these solvents have a property to swell the high-molecular weight compound on the surface of the medical device.

In the present invention, any method which is ordinarily used may be adopted as the coating method. For example, there may be exemplified spin coat, brush painting, and immersing treatment. Preferably, the coating process is performed by means of the immersing treatment.

The reaction between the second reactive functional group possessed by the high-molecular weight compound composed of N-substituted alkylacrylamide and the first reactive functional group existing on the surface of the base material for constructing the medical device is achieved by coating the base material with the high-molecular weight compound composed of N-substituted alkylacrylamide, and then performing heating. The heating temperature is usually within a range of 40° C. to 100° C., and preferably 50° C. to 90° C. The heating time is usually within a range of 60 to 300 minutes, preferably 60 to 240 minutes.

According to the present invention, it is possible to provide the medical device excellent in safety in which the coefficient of friction is small when the medical device is inserted or pierced into a living body, and the elution of the hydrophilic macromolecule existing on the surface of the medical device is suppressed.

DESCRIPTION OF PREFERRED EMBODIMENTS

The present invention will be explained in further detail below with reference to Examples. However, the present invention is not limited to the following Examples, which may take other various forms without deviating from the gist or essential characteristics thereof.

EXAMPLE 1

1.94 g of N,N-dimethylacrylamide and 0.076 g of hydroxyethyl methacrylate (hereinafter abbreviated as "HEMA", if necessary) as a functional group-containing monomer were mixed with 1,4-dioxane containing 0.24% by weight of N,N'-azobisisobutylonitrile. An obtained mixture solution was placed in a sealed tube. The gas phase was substituted with nitrogen, and then the sealed tube was maintained at 70° C. for 4 hours to perform polymerization. A reaction mixture was taken out of the sealed tube. An obtained polymer was precipitated with diethyl ether, followed by drying in vacuum. As a result, 1.9 g of the polymer was obtained.

EXAMPLE 2

1.952 g of N,N-dimethylacrylamide and 0.032 g of hydroxyethyl methacrylate as a functional group-containing monomer were mixed with 1,4-dioxane containing 0.24% by weight of N,N'-azobisisobutylonitrile. The obtained mixture solution was placed in a sealed tube. The gas phase was substituted with nitrogen, and then the sealed tube was maintained at 70° C. for 4 hours to perform polymerization. A reaction mixture was taken out of the sealed tube. An obtained polymer was precipitated with diethyl ether, followed by drying in vacuum. As a result, 1.95 g of the polymer was obtained.

EXAMPLE 3

A urethane film as a base material (produced by Dow Chemical, trade name: "Pellecene") was immersed in a methyl ethyl ketone solution containing 3% by weight of diphenylmethane diisocyanate for 3 minutes, followed by drying in air for 3 minutes. Subsequently, the base material was immersed in a methyl ethyl ketone solution containing 5% of the polymer obtained in Example 1 for 1 minute, followed by drying for 3 minutes. The base material and the polymer were coupled to one another by maintaining the materials for 3 hours in a hot air drier at 80° C. When the surface of an obtained coating was observed with an optical microscope, fine irregularities were found. The coefficient of dynamic friction with respect to a stainless steel surface was measured in water by using a friction meter (automatic friction/wearing analyzer "DFPM-SS Type" produced by Kyowa Interface Scientific). The coefficient of friction was 0.030 which was low. The coefficient of friction was not changed even after being maintained for 1 week in water. No peeled-off coating was observed even after being rubbed with fingers.

Summarized results are shown in Table 1. The property of the surface shown in the table is represented as follows; A: there were few irregularities on the surface of the coating, B: fine irregularities were found on the surface of the coating, and C: cracks appeared on the coating.

EXAMPLE 4

Experiment was carried out in the same manner as in Example 3 except that the polymer obtained in Example 2 was used in place of the polymer obtained in Example 1. Fine irregularities were found on the surface of the coating. The coefficient of dynamic friction was 0.032. The coefficient of friction was not changed even after being maintained in water for 1 week. No peeled-off coating was observed even after being rubbed with fingers.

COMPARATIVE EXAMPLE 1

Experiment was carried out in the same manner as in Example 3 except that poly(N-vinylpyrrolidone) (produced by BASF, trade name: "Povidone K-90") was used in place of the polymer obtained in Example 1. The coefficient of dynamic friction obtained immediately after being placed in water was 0.08. However, when the obtained product was maintained in water for 1 week, peeled-off coating was observed. The coating was easily peeled off when it was merely rubbed with fingers.

COMPARATIVE EXAMPLE 2

Experiment was carried out in the same manner as in Example 3 except that a copolymer of maleic anhydride and methyl vinyl ether (produced by ISP Investment, trade name: "GANTREZ AN-169") was used in place of the polymer obtained in Example 1. The coefficient of dynamic friction obtained immediately after being placed in water was 0.07. However, when the obtained product was maintained in water for 1 week, peeled-off coating was observed. The coating was easily peeled off when it was merely rubbed with fingers.

EXAMPLE 5

2.005 g of N,N-dimethylacrylamide and 0.0067 g of hydroxyethyl methacrylate as a functional group-containing monomer were mixed with 1,4-dioxane containing 0.1% by weight of N,N'-azobisisobutylonitrile. An obtained mixture solution was placed in a sealed tube. The gas phase was substituted with nitrogen, and then the sealed tube was maintained at 70° C. for 7 hours. A reaction mixture was taken out of the sealed tube. An obtained polymer was precipitated with diethyl ether, followed by drying in vacuum. As a result, 1.95 g of the polymer was obtained.

EXAMPLE 6

A urethane film as a base material (produced by Dow Chemical, trade name: "Pellecene") was immersed in a methyl ethyl ketone solution containing 3% by weight of methylene diisocyanate for 1 minute. After that, the base material was taken out of the solution, followed by drying in air for 3 minutes. Subsequently, the base material was immersed in a methyl ethyl ketone solution containing 5% of the polymer obtained in Example 5 for 15 seconds, followed by drying in air for 3 minutes. After drying at 60° C. for 1 hour in a hot air drier, the base material and the polymer were coupled to one another by maintaining the materials for 1 hour in a hot air drier at 80° C.

was coupled to the urethane film in the same manner as in Example 6. Physical properties were measured in the same manner as in Example 3. Results are shown in Table 1.

EXAMPLES 10 AND 11

Experiment was carried out in the same manner as in Example 9 except that the amounts of N,N-dimethylacrylamide and acrylamide were changed as shown in Table 1. Results are shown in Table 1.

TABLE 1

|  | Functional group-containing monomer | | Flexibility-adding monomer | | Coefficient of static friction | Coefficient of dynamic friction | Surface property |
| --- | --- | --- | --- | --- | --- | --- | --- |
|  | Type | mol % | Type | mol % |  |  |  |
| Ex. 1,3 | HEMA | 2.90 | NON | — | — | 0.030 | B |
| Ex. 2,4 | HEMA | 1.23 | NON | — | — | 0.032 | B |
| Ex. 5,6 | HEMA | 0.25 | NON | — | 0.023 | 0.017 | B |
| Ex. 7 | HEMA | 0.50 | NON | — | 0.028 | 0.018 | B |
| Ex. 8 | HEMA | 1.01 | NON | — | 0.032 | 0.025 | B |
| Ex. 9 | AAM | 0.98 | NON | — | 0.0255 | 0.0213 | B |
| Ex. 10 | AAM | 1.95 | NON | — | 0.0202 | 0.0135 | B |
| Ex. 11 | AAM | 3.92 | NON | — | 0.0003 | 0.0000 | B |

HEMA: hydroxyethyl methacrylate
AAM: acrylamide

The coefficient of friction with respect to stainless steel in water was measured in the same manner as in Example 3. As a result, the coefficient of dynamic friction was 0.017, and the coefficient of static friction was 0.023. The coefficient of friction was not changed even after being maintained for 1 week in water. No peeled-off coating was observed even after being rubbed with fingers. The surface of the coating was observed in the same manner as in Example 3. As a result, fine irregularities were found on the surface of the coating. Summarized results are shown in Table 1.

EXAMPLES 7 AND 8

Experiment was carried out in the same manner as in Example 5 except that the amounts of N,N-dimethylacrylamide and hydroxyethyl methacrylate were changed as shown in Table 1. An obtained polymer was coupled to the urethane film in accordance with the same method as used in Example 6. Physical properties were measured in the same manner as in Example 3. Results are shown in Table 1.

EXAMPLE 9

1.9928 g of N,N-dimethylacrylamide and 0.0142 g of acrylamide (hereinafter abbreviated as "AAM", if necessary) as a functional group-containing monomer were mixed with 3 g of 1,4-dioxane containing 0.1% by weight of N,N'-azobisisobutylonitrile. An obtained mixture solution was placed in a sealed tube. The gas phase was substituted with nitrogen, and then the sealed tube was maintained at 70° C. for 7 hours. A reaction mixture was taken out of the sealed tube. An obtained polymer was precipitated with diethyl ether, followed by drying in vacuum. As a result, 1.87 g of the polymer was obtained. The obtained polymer

EXAMPLE 12

1.9097 g of N,N-dimethylacrylamide, 0.0484 g of hydroxyethyl methacrylate as a functional group-containing monomer, and 0.0344 g of diacetone acrylamide as a flexibility-adding monomer were mixed with 3 g of 1,4-dioxane containing 0.1% by weight of N,N'-azobisisobutylonitrile. An obtained mixture solution was placed in a sealed tube. The gas phase was substituted with nitrogen, and then the sealed tube was maintained at 70° C. for 7 hours. A reaction mixture was taken out of the sealed tube. An obtained polymer was precipitated with diethyl ether, followed by drying in vacuum. As a result, 1.9137 g of the polymer was obtained. The obtained polymer was coupled to the urethane film in the same manner as in Example 6. Physical properties were measured in the same manner as in Example 3. Results are shown in Table 2.

EXAMPLES 13 TO 19

Experiment was carried out in the same manner as in Example 12 except that the amounts of N,N-dimethylacrylamide, hydroxyethyl methacrylate, and diacetone acrylamide were changed as shown in Table 2. Results are shown in Table 2.

TABLE 2

| | Functional group-containing monomer | | Flexibility-adding monomer | | Coefficient of static friction | Coefficient of dynamic friction | Surface property |
|---|---|---|---|---|---|---|---|
| | Type | mol % | Type | mol % | | | |
| Ex. 12 | HEMA | 1.88 | DAA | 1.02 | 0.036 | 0.019 | A |
| Ex. 13 | HEMA | 1.87 | DAA | 1.97 | 0.038 | 0.016 | A |
| Ex. 14 | HEMA | 1.96 | DAA | 4.05 | 0.033 | 0.016 | A |
| Ex. 15 | HEMA | 1.92 | DAA | 7.99 | 0.035 | 0.021 | A |
| Ex. 16 | HEMA | 0.51 | DAA | 0.49 | 0.019 | 0.007 | A |
| Ex. 17 | HEMA | 0.53 | DAA | 1.04 | 0.016 | 0.004 | A |
| Ex. 18 | HEMA | 0.50 | DAA | 1.97 | 0.016 | 0.005 | A |
| Ex. 19 | HEMA | 0.51 | DAA | 3.94 | 0.017 | 0.006 | A |

DAA: diacetone acrylamide

EXAMPLES 20 TO 31

Experiment was carried out in the same manner as in Example 9 by using N,N-dimethylacrylamide except that hydroxyethyl methacrylate was used as a functional group-containing monomer, any one of acrylic acid, ethyl acrylate, and vinyl acetate was used as a flexibility-adding monomer, and the amounts of the respective components were changed as shown in Table 3 and Table 4. Results are shown in Table 3 and Table 4.

TABLE 3

| | Functional group-containing monomer | | Flexibility-adding monomer | | Coefficient of static friction | Coefficient of dynamic friction | Surface property |
|---|---|---|---|---|---|---|---|
| | Type | mol % | Type | mol % | | | |
| Ex. 20 | HEMA | 0.64 | AcA | 1.98 | 0.0059 | 0.0013 | A |
| Ex. 21 | HEMA | 0.50 | AcA | 4.01 | 0.0126 | 0.0066 | A |
| Ex. 22 | HEMA | 0.49 | EA | 0.96 | 0.007 | 0.001 | A |
| Ex. 23 | HEMA | 0.51 | EA | 4.04 | 0.005 | 0.001 | A |
| Ex. 24 | HEMA | 0.50 | EA | 8.29 | 0.011 | 0.005 | A |

AcA: acrylic acid
EA: ethyl acrylate

TABLE 4

| | Functional group-containing monomer | | Flexibility-adding monomer | | Coefficient of static friction | Coefficient of dynamic friction | Surface property |
|---|---|---|---|---|---|---|---|
| | Type | mol % | Type | mol % | | | |
| Ex. 25 | HEMA | 0.49 | VAc | 0.91 | 0.006 | 0.001 | A |
| Ex. 26 | HEMA | 0.49 | VAc | 4.09 | 0.030 | 0.022 | A |
| Ex. 27 | HEMA | 0.50 | VAc | 8.12 | 0.020 | 0.016 | A |
| Ex. 28 | HEMA | 0.29 | VAc | 1.17 | 0.014 | 0.010 | A |
| Ex. 29 | HEMA | 0.29 | VAc | 0.59 | 0.017 | 0.012 | A |
| Ex. 30 | HEMA | 0.29 | VAc | 2.28 | 0.020 | 0.013 | A |
| Ex. 31 | HEMA | 0.32 | VAc | 4.34 | 0.018 | 0.012 | A |

EXAMPLES 32 TO 37

Experiment was carried out in the same manner as in Example 9 by using N,N-dimethylacrylamide except that hydroxyethyl methacrylate was used as a functional group-containing monomer, methyl methacrylate or hexyl methacrylate was used as a flexibility-adding monomer, and the amounts of the respective components were changed as shown in Table 5. Results are shown in Table 5.

TABLE 5

| | Functional group-containing monomer | | Flexibility-adding monomer | | Coefficient of static friction | Coefficient of dynamic friction | Surface property |
|---|---|---|---|---|---|---|---|
| | Type | mol % | Type | mol % | | | |
| Ex. 32 | HEMA | 0.50 | MMA | 1.26 | 0.005 | 0 | A |
| Ex. 33 | HEMA | 0.49 | MMA | 2.03 | 0.006 | 0 | A |
| Ex. 34 | HEMA | 0.52 | MMA | 4.00 | 0.005 | 0 | A |
| Ex. 35 | HEMA | 0.50 | HXMA | 1.06 | 0.009 | 0.002 | A |
| Ex. 36 | HEMA | 0.49 | HXMA | 2.17 | 0.013 | 0.004 | A |
| Ex. 37 | HEMA | 0.52 | HXMA | 4.34 | 0.019 | 0.002 | A |

MMA: methyl methacrylate
HXMA: hexyl methacrylate

COMPARATIVE EXAMPLE 3

11.1 parts by weight of N-vinylpyrrolidone and 0.205 part by weight of 2-hydroxyethyl methacrylate were placed in a reaction vessel equipped with an agitator, a ball cooling tube, and a nitrogen-introducing tube, and the content was diluted with 25 parts by weight of methyl alcohol. The reaction vessel was maintained at 70° C. under a nitrogen flow, to which 5 parts by weight of methyl alcohol containing 0.05 part by weight of azobisisobutyronitrile was added. The reaction vessel was maintained at 70° C. for 6 hours while being subjected to agitation and reflux. Methyl alcohol was distilled off, and the content was dried in vacuum. An obtained polymer was dissolved in 25 parts by weight of dimethylformamide, and it was diluted with 25 parts by weight of dichloromethane.

COMPARATIVE EXAMPLE 4

A urethane film as a base material (produced by Dow Chemical, trade name: "Pellecene") was immersed in a dichloromethane solution containing 3% by weight of diphenylmethane diisocyanate for 1 minute, followed by drying in air for 10 minutes. The base material was immersed in a solution of the polymer obtained in Comparative Example 3 for 30 seconds, followed by drying in air for 10 minutes. After that, the base material was maintained at 100° C. for 20 minutes in a hot air drier, followed by drying in vacuum at 60° C. for 5 hours. The coefficient of friction in water of the obtained film was measured in the same manner as in Example 3. As a result, both of the coefficient of static friction and the coefficient of dynamic friction were 0.12. The obtained film was immersed in water for 1 week, and then the coefficient of static friction and the coefficient of dynamic friction were measured again in water. As a result, any of them increased to 0.21.

COMPARATIVE EXAMPLE 5

A urethane film as a base material (produced by Dow Chemical, trade name: "Pellecene") was immersed in methyl ethyl ketone for 20 seconds. Subsequently, the base material was immersed in a dichloromethane solution containing 10% by weight of diphenylmethane diisocyanate for 20 seconds, followed by drying in air for 3 minutes. The base material was immersed for 40 seconds in a dichloromethane solution containing 5% by weight of polyethylene glycol (produced by Tokyo Kasei, molecular weight: 20,000), and then it was maintained at room temperature for 50 hours.

The coefficient of friction in water was measured after being maintained in water for 6 hours, in the same manner as in Example 3. As a result, the coefficient of static friction was 0.10, and the coefficient of dynamic friction were 0.10.

EXAMPLE 38

A urethane film as a base material (produced by Dow Chemical, trade name: "Pellecene") was immersed in a methyl ethyl ketone solution containing 1% by weight of diphenylmethane diisocyanate for 1 minute. After that, the base material was taken out of the solution, followed by drying in hot air at 60° C. for 1 hour. Subsequently, the base material was immersed in a methyl ethyl ketone solution containing 10% of the polymer obtained in Example 9 for 30 seconds, followed by drying in air for 3 minutes. The base material and the polymer were coupled to one another by maintaining the materials for 2 hours in a hot air drier at 80° C. Surface physical properties were measured in the same manner as in Example 3. As a result, the coefficient of dynamic friction in water was 0.005, and the coefficient of static friction was 0.007.

EXAMPLES 39 TO 42

Experiment was carried out in the same manner as in Example 38 except that the concentration of the methyl ethyl ketone solution of diphenylmethane diisocyanate was changed as shown in Table 6. Surface physical properties are shown in Table 6.

TABLE 6

| | Concentration of methyl ethyl ketone solution of diphenylmethane diisocyanate (wt %) | Coefficient of static friction | Coefficient of dynamic friction |
|---|---|---|---|
| Example 39 | 0.5 | 0.004 | 0.003 |
| Example 40 | 2 | 0.017 | 0.014 |
| Example 41 | 3 | 0.012 | 0.01 |
| Example 42 | 5 | 0.01 | 0.009 |

EXAMPLE 43

A urethane film as a base material (produced by Dow Chemical, trade name: "Pellecene") was immersed in a methyl ethyl ketone solution containing 2% by weight of diphenylmethane diisocyanate for 1 minute. After that, the base material was taken out of the solution, followed by drying in hot air at 60° C. for 1 hour. Subsequently, the base material was immersed in a methyl ethyl ketone solution containing 10% of the polymer obtained in Example 10 for 15 seconds, followed by drying in air for 3 minutes. The base material and the polymer were coupled to one another by maintaining the materials for 2 hours in a hot air drier at 60° C. Surface physical properties were measured in the same manner as in Example 3. As a result, the coefficient of dynamic friction in water was 0.008, and the coefficient of static friction was 0.013.

EXAMPLES 44, 45

Experiment was carried out in the same manner as in Example 39 except that the immersing time in the methyl ethyl ketone solution of diphenylmethane diisocyanate was changed as shown in Table 7. Surface physical properties are shown in Table 7.

TABLE 7

| | Immersing time in methyl ethyl ketone solution of diphenylmethane diisocyanate (min) | Coefficient of static friction | Coefficient of dynamic friction |
|---|---|---|---|
| Example 44 | 3 | 0.006 | 0.001 |
| Example 45 | 5 | 0.026 | 0.015 |

EXAMPLE 46

A urethane film as a base material (produced by Dow Chemical, trade name: "Pellecene") was immersed in a methyl ethyl ketone solution containing 2% by weight of diphenylmethane diisocyanate for 1 minute. After that, the base material was taken out of the solution, followed by drying in hot air at 60° C. for 1 hour. Subsequently, the base material was immersed in a methyl ethyl ketone solution containing 2% of the polymer obtained in Example 9 for 15 seconds, followed by drying in air for 3 minutes. The base material and the polymer were coupled to one another by maintaining the materials for 2 hours in a hot air drier at 60° C. Surface physical properties were measured in the same manner as in Example 3. As a result, the coefficient of dynamic friction in water was 0.009, and the coefficient of static friction was 0.023.

EXAMPLE 47

Experiment was carried out in the same manner as in Example 42 except that a methyl ethyl ketone solution containing 10% of the polymer obtained in Example 9 was used. Surface physical properties were measured in the same manner as in Example 3. As a result, the coefficient of dynamic friction in water was 0.003, and the coefficient of static friction was 0.009.

We claim:

1. A medical device comprising a base material for constructing the medical device, and a high-molecular weight compound composed of N-substituted alkylacrylamide coupled to a surface of the base material by the aid of chemical bond, wherein the chemical bond is formed by a reaction between a first reactive functional group which is an isocyanate group and a second reactive functional group which is reactive with the first reactive functional group, wherein the first reactive functional group originates from the surface of the base material, and the second reactive functional group originates from the high-molecular weight compound composed of the N-substituted alkylacrylamide.

2. The medical device according to claim 1, wherein the high-molecular weight compound composed of N-substituted alkylacrylamide is a copolymer containing, as a monomer unit, N-substituted alkylacrylamide and at least one monomer selected from the group consisting of hydroxyethyl methacrylate, hydroxyethyl acrylate, and acrylamide.

3. The medical device according to claim 1, wherein the high-molecular weight compound composed of N-substituted alkylacrylamide is a copolymer containing, as a monomer unit, hydroxyethyl methacrylate and N-substituted alkylacrylamide.

4. The medical device according to claim 3, wherein the high-molecular weight compound composed of N-substituted alkylacrylamide is a copolymer containing, as a monomer unit, at least one monomer selected from the group consisting of diacetone acrylamide, acrylic acid, methacrylic acid, ester of acrylic acid and alcohol having a number of carbon or carbons of 1 to 12, ester of methacrylic acid and alcohol having a number of carbon or carbons of 1 to 12, and vinyl ester.

5. The medical device according to claim 2, wherein the high-molecular weight compound composed of N-substituted alkylacrylamide contains, as a monomer unit, at least one monomer selected from the group consisting of diacetone acrylamide, methyl methacrylate, and ethyl acrylate.

6. The medical device according to claim 1, wherein the N-substituted alkylacrylamide has an alkyl group having a number of carbon or carbons of 1 to 4.

7. The medical device according to claim 1, wherein the N-substituted alkylacrylamide is N,N-dimethylacrylamide.

8. The medical device according to claim 1, wherein the high-molecular weight compound composed of N-substituted alkylacrylamide contains, as a monomer unit, at least one monomer selected from the group consisting of N,N-dimethylacrylamide, hydroxyethyl methacrylate, diacetone acrylamide, methyl methacrylate and ethyl acrylate.

9. The medical device according to claim 1, wherein the medical device is adapted to contact with tissue of a living body.

10. The medical device according to claim 1, wherein the medical device is a catheter.

11. The medical device according to claim 9, wherein the tissue of a living body is selected from the group consisting of mucous membrane and blood.

12. The medical device according to claim 1, wherein said second reactive functional group is a hydroxyl, amino or carboxyl group.

* * * * *